United States Patent [19]

Renirie

[11] 4,031,899

[45] June 28, 1977

[54] LONG LIFE CARDIAC PACER WITH SWITCHING POWER DELIVERY MEANS AND METHOD OF ALTERNATELY DELIVERING POWER TO RESPECTIVE CIRCUIT PORTIONS OF A STIMULUS DELIVERY SYSTEM

[75] Inventor: Alexis C. M. Renirie, Dieren, Netherlands

[73] Assignee: Vitatron Medical B.V., Dieren, Netherlands

[22] Filed: Jan. 22, 1976

[21] Appl. No.: 651,549

[52] U.S. Cl. .......................................... 128/419 PS
[51] Int. Cl.[2] ........................................ A61N 1/36
[58] Field of Search ... 128/419 E, 419 PG, 419 PS, 128/419 R, 421, 422, 423

[56] References Cited

UNITED STATES PATENTS

| | | |
|---|---|---|
| 3,433,228 | 3/1969 | Keller, Jr. .................... 128/419 PG |
| 3,547,127 | 12/1970 | Anderson .................... 128/419 PG |
| 3,563,247 | 2/1971 | Bowers ........................ 128/419 PG |
| 3,667,477 | 6/1972 | Susset et al. ................. 128/419 E |
| 3,866,614 | 2/1975 | Svensson ..................... 128/419 PG |
| 3,893,463 | 7/1975 | Williams ........................ 128/421 |
| 3,898,994 | 8/1975 | Kolgnik et al. .............. 128/419 PG |
| 3,926,197 | 12/1975 | Allex ............................ 128/419 PG |

*Primary Examiner*—William E. Kamm
*Attorney, Agent, or Firm*—Woodcock, Washburn, Kurtz & Mackiewicz

[57] ABSTRACT

A pacer having a DC to DC converter for use with a relatively low voltage power source, and for providing a raised voltage supply to a load characterized by having a first circuit portion which is voltage sensitive and draws a low current, and a second circuit portion which draws a high current and is relatively insensitive to supply deviations, comprising a switching circuit alternately connecting said respective circuit portions through respective converters to the supply so that the voltage sensitive circuit is not affected by the loading of the high current circuit. A method is provided for alternately delivering power from a battery source to respective circuit portions of a stimulus delivery system.

38 Claims, 12 Drawing Figures

_Fig. 10_

_Fig. 11_

LONG LIFE CARDIAC PACER WITH SWITCHING POWER DELIVERY MEANS AND METHOD OF ALTERNATELY DELIVERING POWER TO RESPECTIVE CIRCUIT PORTIONS OF A STIMULUS DELIVERY SYSTEM

BACKGROUND OF THE INVENTION

1. Field of the Invention

This invention relates to pacers having DC power connecting circuits, and, more particularly, to pacer switching circuits adapted to switchably deliver power from a low power source to a plurality of circuits so as to match the respective circuit requirements to the source characteristics. In the case of low voltage level DC sources, the power connecting circuit may also comprise one or more converter circuits for raising the delivered voltage level.

2. Description of the Prior Art

The cardiac pacer field is now over a decade old, and great strides have been made in improving the characteristics and reliability of pacers for permanent implant in patients. The improvements in the pacer field have come both from improvements in the components which can be used in pacers, such as CMOS devices and other forms of microelectronics, and from improved designs for providing better pacing stimulus production and more reliability. To date, the most significant improvements which have resulted in greater lifetime for an implanted pacer have occurred from circuit improvements which provide for a lower power drain, as well as electrode improvements which permit effective stimulation of the heart with lower output pulses. For the most part during the history of pacer development, there has been relatively little improvement in the battery sources themselves, such that pacer lifetime for most models has been between about 18 months and 36 months. Even with the most advanced hybrid designs which have appeared to date, the current drain causes such a depletion in conventional cells that a lifetime of more than 3 years has not been expected in most models, and is not relied upon by the physician.

However, within recent times new battery sources have become available, and more importantly have been tested to the point where they are being accepted by the industry as reliable. For example, lithium-iodide battery cells are now becoming available from at least several manufacturers, and such cells offer a promise of a lifetime of greater than 5 years, depending of course upon the power drain of the pacer which is being driven. In addition, other types of sources including nuclear sources are becoming available and are gaining acceptance in the industry. Such new power sources give rise to the possibility that reliable and relatively lightweight pacers can be made available, and at an expense not markedly greater than present day models, having lifetimes which are appreciable compared to the statistical expected lifetimes of the patients receiving pacer implants. Studies suggest that the average lifetime of a patient at the time he first receives a pacer implant is approximately five years, and in this light it is recognized that a pacer using a battery source such a lithium iodide cell which could provide a reliable lifetime of 5 to 10 years would be an outstanding achievement and of inestimable value to a patient receiving such pacer.

While nuclear powered pacers are believed to be feasible having lifetimes in the order of 30 years, such pacers are many times more expensive, and are advisable only for the smaller class of patients where implant are required at a young enough age such that the statistical expected lifetime approaches the lifetime of the pacer source. For the great percentage of the anticipated pacer market, i.e., more than 90%, a pacer which could provide a reliable lifetime of 8 or more years would be considered to be optimum from the standpoint of economy and simplicity. However, when the characteristics of the new battey cells are matched with the electrical requirements of pacers, it is seen that for most pacers the full potential of the newer cells simply is not realizable, primarily because after about 5 years the changing characteristics of the cells produce an altered pacer operation. If such altered operation falls below allowable limits, the pacer has to be removed from the patient even though it may have an appreciable amount of energy left within it.

A first primary characteristic of the lithium-iodide cell is that its maximum voltage output is 2.8 volts. The chemical nature of such a cell provides that in terms of electrical characteristics it presents an ideal 2.8 volt source, in combination with an internal resistance. While the 2.8 volt source remains a fixed constant due to the chemistry of the cell, the internal resistance may and indeed does vary as a function of energy delivered by the battery, i.e., its energy depletion. Roughly speaking, such internal resistance increases linearly with energy depletion until a knee in the curve is reached wherein the internal resistance rises dramatically, at which point the useful life of the source is over very soon. However, if in fact the cell can be utilized throughout the full extent of the linear range of relatively low resistance, and utilized throughout the full extent of this range, then its lifetime can be maximized. It is noted that in this specification the example of the lithium-iodide cell is used for illustrative purposes. For purposes of brevity, the term lithium cell, or lithium battery, is used to denote lithium-iodide, lithium-silver chromate, and other cells of such class. It is to be noted, however, that other types of cells are included as well within the invention, and while they may have differing characteristics, the basic characteristics of the cells are sufficiently similar such that the principles of this invention are applicable. For the lithium-iodide cell, a top voltage of 2.8 volts means that for practical purposes a voltage converter device is required in order to raise the available voltage level to a level which provides a safe voltage for circuit operation. While many modern electronic circuits can be designed to operate at less than 2.8 volts, such a requirement imposes severe design limitations, which limitations drastically increase the required complexity of the pacer circuitry and consequently reduce the resulting reliability. Certain circuits simply require a minimum voltage, such as some CMOS devices which require at least 2.4 volts for operation. Even though such circuits could in fact be utilized, the margin of safety would be virtually negligible, such that a relatively small percentage of energy depletion of the battery source would reduce the voltage to a point where reliable circuit operation would no longer be expected.

Another fixed parameter of present day pacer design is that the pulse generator, or oscillator, which provides the stimulus pulses is inherently a voltage sensitive circuit. By that it is meant that the frequency and/or the pulse width of the oscillator vary as a function of the voltage supply. This is the case both because the oscillator circuits which have been found to be reliable for pacer use are of this nature, and because of the presently accepted philosophy of designing the oscillator to be voltage sensitive so as to produce an indication of the battery condition. In accordance with this philosophy, most pacers have provision for external monitoring of the pacer, such as by magnetic coupling devices, whereby the patient or a physician determines the pulse repetition rate and from this information obtains a reading of the depletion condition of the battery. This design feature is sufficiently widely accepted that it can be stated that the voltage sensitive oscillator circuit is at the present a fixed parameter in the pacer industry.

Considering the above factors which influence the design of a pacer, and seeking to determine a design for best utilization of a lithium type battery source, it is noted that conceptually the pacer circuitry can be divided into a first source sensitive, or voltage sensitive circuit which includes the pacer oscillator, and a second circuit which is not as critically sensitive to the source output, or source condition, such second circuit portion including the output pulse circuit. In a typical example, the steady state current drain for an entire pacer may be about 25 microamps, such drain being accounted for by approximately a 5 microamp current drain through the amplifier, logic and oscillator portions of the pacer circuitry, and the remaining 20 microamps being accounted for by the stimulus pulse outputs. The output circuit thus represents a relatively high power drain to the battery, and when it draws current it acts to produce a voltage drop across the internal resistance of the source, which in turn causes a corresponding voltage drop in the voltage level delivered to the low current drain voltage sensitive portion of the pacer. The problem is that the loading of the source caused by the output circuit produces a voltage drop which is relatively unacceptable when applied to the voltage sensitive circuit. In conventional designs the voltage delivered to the output circuit is the same as to the oscillator circuit, and may be permitted to drop to a certain level without dangerous impairment of pacer operation. Indeed, many circuits are now being incorporated into pacers to lengthen the pulse width of the stimulus output to counteract decreasing pulse current. However, the loading effect of the stimulus pulses on the voltage supplied to the oscillator becomes more severe with battery depletion, and it is clear that there is a limit to the tolerable drop in oscillator frequency. Thus, conventional design provides that the oscillator frequency be the controlling variable, and the pacer is considered to be at the end of its useful life when its frequency drops by a predetermined amount. In fact, it is now understood that the battery source under such circumstances still retains a great amount of energy, and in particular an amount which could provide substantial continued operation. It is the failure of the circuit designs as used to date that leaves this residual amount of energy unused and that causes relatively premature removal of the pacer.

An alternate approach which has been considered as a solution to the above problem is to convert the available DC level to a level which is sufficiently high that it can be regulated to a somewhat lower level, the difference between the higher converted level and the regulated level providing a margin of safety which permits battery depletion while the voltage supplied to the circuitry is stabilized. For example, using this approach and a source which provides an initial voltage of 2.8 volts, the voltage level may be converted by a factor of 3 to about 8.4, and then regulated or stabilized down to about 6 or 6.5 volts. With this arrangement, until the effective battery output drops to the regulation voltage, no change is seen at the pacer circuitry. However, this arrangement has the distinct disadvantage that the regulator must dissipate a substantial amount of the battery energy in reducing the voltage to the stabilized level. In particular, and for the figures used in this illustration, at the initial starting of the lifetime of the pacer approximately 25 to 30% of the power being delivered by the battery would be dissipated across the regulator. Quite clearly, where extending the lifetime of the pacer is the design goal, it is not desirable to toss away this amount of power. In addition, this arrangement has the drawback that as long as the regulator is putting out a fixed voltage, there is no indication of battery change available, and only when the source is depleted to the point where the available voltage drops below the regulator voltage is there any indication. Of course, at the time that this indication is provided, then the patient is faced with a virtual crisis situation, since a new pacer must be implanted rather quickly.

In consideration of the above, it is seen that there is required a very thorough understanding of the optimum manner of utilizing the available energy from the newer longer life battery cells which are becoming available. What is called for is a circuit design which provides an optimum interface between the operating portions of the pacer circuitry and the battery, the interface being designed so as to provide for power delivery to the different circuit portions in a manner which optimizes the overall pacer operation.

SUMMARY OF THE INVENTION

It is an object of this invention to provide an improved pacer design utilizing a relatively low voltage source, which source has characteristics which change as a function of its energy depletion, and having a reliable circuit for providing energy to the pacer at voltage levels which optimize pacer performance, and in particular pacer lifetime.

It is another object of this invention to provide, in an implantable cardiac pacer, means for transferring power from a low voltage source separately to respective circuit portions of the pacer in a manner so as to achieve greater utilization of the available source energy.

It is another object of this invention to provide power delivery means for delivering power one or more sources to a plurality of circuits, the delivery means being designed to match the differing power requirements of the respective circuits to the one or more sources.

In is another object of this invention to provide an implantable type cardiac pacer device utilizing a battery source which has characteristics which vary as a function of energy which has been delivered from such source, the pacer being designed to optimally interface the pacer circuitry with such source to extend the useful pacer lifetime.

It is another object of this invention to provide a cardiac pacer having a voltage sensitive circuit portion, the pacer providing a power supply with a programmed voltage level for powering such voltage sensitive portion.

It is a still further object of this invention to provide long life apparatus utilizing a low level DC power source and having circuitry for providing output signals of a predetermined nature, the apparatus having a conversion circuit for converting the DC level of the source to a higher DC level, the conversion characteristics of the converter being predetermined to vary as a function of the energy depletion of the source.

It is another object of this invention to provide a method for alternately delivering energy from a DC source to respective circuit portions of a biomedical stimulus delivery system.

It is a still futher object of this invention to provide, in a cardiac pace for providing stimular pulses for pacing of a human patient, a power source and respective circuit portions which draw respective different loads from such power source, and circuitry for operatively connecting such source to such respective circuit portions to provide separate effective power supplies to such respective portions, the source being operatively connected at separate times so that the relatively high current portions of the pacer circuit have a minimal loading effect on the source at the time of delivery of power to the relatively low current portions of the circuit.

In view of the above objects, there is provided apparatus containing a source having characteristics which vary as a function of the power which has been delivered from such source, and at least two circuit portions, a first being a voltage sensitive circuit characterized by operating in a manner which is dependent upon the voltage level provided from the source and being inherently a relatively low current drain circuit, the second circuit portion being a relatively high current load, and delivery circuitry driven by the source for delivering power from said source respectively to said voltage sensitive circuit and said relatively high current load, the delivery circuit delivering power to said circuit portions independently and in a manner which minimizes the loading effect of the high current circuit on the voltage level delivered to the voltage sensitive circuit. The delivery circuitry may comprise a converting circuit for converting the DC output of the source to a higher DC level, the conversion characteristic being a function of the power condition of the source.

DESCRIPTION OF THE PREFERRED EMBODIMENTS

Figure 1:
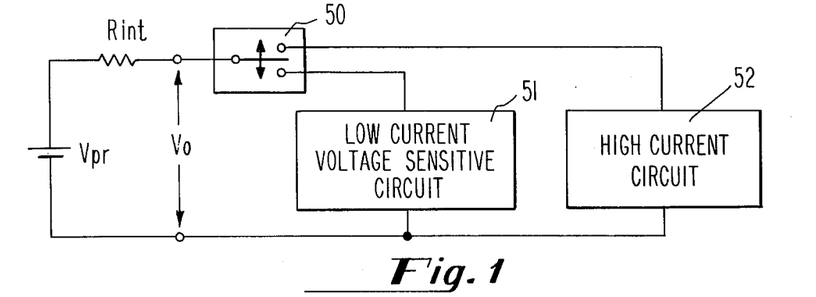
FIG. 1 is a block diagram showing the basic switching arrangement of the apparatus of this invention.
Figure 5:
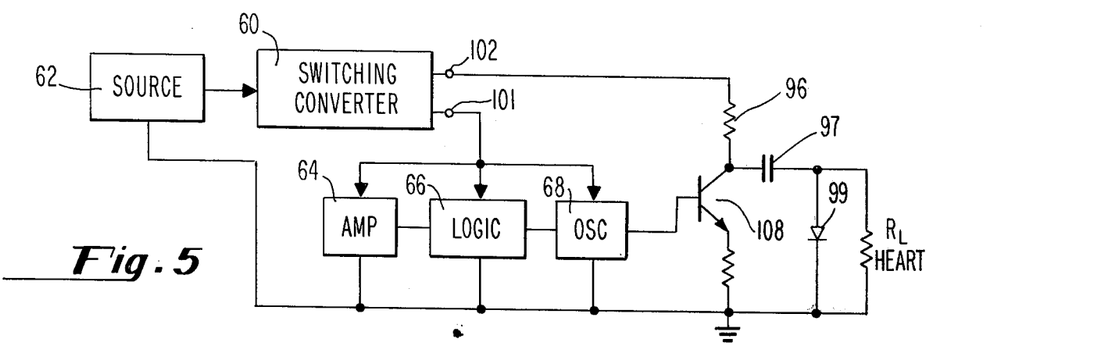
FIG. 5 is a block diagram of a cardiac pacer which includes the converter/switching circuit of FIG. 3.
Figure 6:
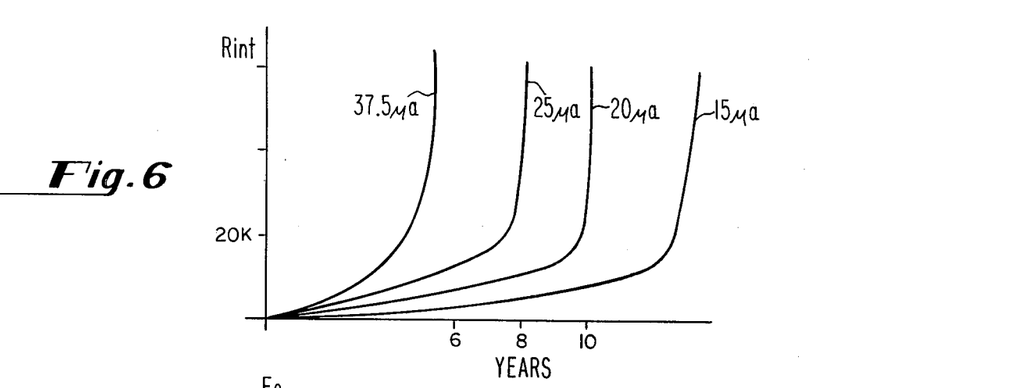
FIG. 6 is a first set of curves illustrating typical characteristics of a source as utilized in this invention.

Referring to the drawings, there is shown in FIG. 1 a block diagram of the basic switching arrangement of the preferred embodiment of this invention. A power source is indicated as having an ideal voltage designated $V_{pr}$ and an internal resistance designated as $R_{int}$. As mentioned previously, for a lithium type cell $V_{pr}$ is fixed in the amount of 2.8 volts. $R_{int}$, as seen in FIG. 6, may vary between appreciably 0 ohms when new to a resistance in excess of 100 K. In fact, the battery source may also have a very small effective capacitance across its terminals, which would contribute to its internal impedance. For the description to follow, it is presumed that such capacitance is sufficiently negligible to ignore, but the term internal resistance is used as embracing any internal reactive component of the source as well. The output of the source is connected to block 50 which is shown in FIG. 1 as being an idealized switch. The switch has two outputs, a first connecting the source to a low current voltage sensitive circuit 51, and the second connecting the source to a relatively high current circuit 52. In the device of this invention as utilized in a pacer, block 51 includes the stimulus signal oscillator, which has a frequency which varies as a function of the voltage supply connected to it. As shown in FIG. 5, the low current circuit may also comprise the amplifier and logic circuitry. The amplifier 64 and logic circuitry 66 may in fact be substantially insensitive to voltage variations, as for example in the apparatus disclosed in my co-pending application Ser. No. 608,465, filed Aug. 28, 1975, assigned to the same assignee, which is incorporated herein by reference. For this reason, the voltage sensitive circuit, or source sensitive circuit, is defined as a circuit which comprises at least in part a voltage sensitive circuit such as the oscillator of a Pacemaker. Correspondingly, the high current circuit 52 may comprise portions which are relatively low current circuits, but comprises as well a high current portion such as the stimulus pulse output circuit of a pacer. In the ideal system of FIG. 1, the switching circuit 50 is powered by the source and connects the source to only one circuit portion or the other at any given time. Since the low current circuit 51 draws power only when the high current circuit is not connected to the source, the voltage $V_o$ supplied from the source is substantially constant at $V_{pr}$, due to the very low current drive across $R_{int}$. In this arrangement, each of circuits 51 and 52 must tank up on power during the time when connected to the source, but at the given instant when the low current voltage sensitive circuit is drawing power, the effect on the source of the high current circuit is eliminated, such that the depletion of the source by the high current circuit is substantially unseen by the low current circuit. For example, if the low current circuit draws less than 5 microamps, during the operating life of the source while its $R_{int}$ grows from about 0 to 20K ohm, the effective output $V_o$ of the source was seen by circuit 51 drops only from 2.8 volts to 2.7 volts. At the same time, for a current drain of 20 microamps through the high current circuit, presuming this to be a DC current, then the output voltage drops by 4 times as much, or to 2.4 volts.

Figure 2:
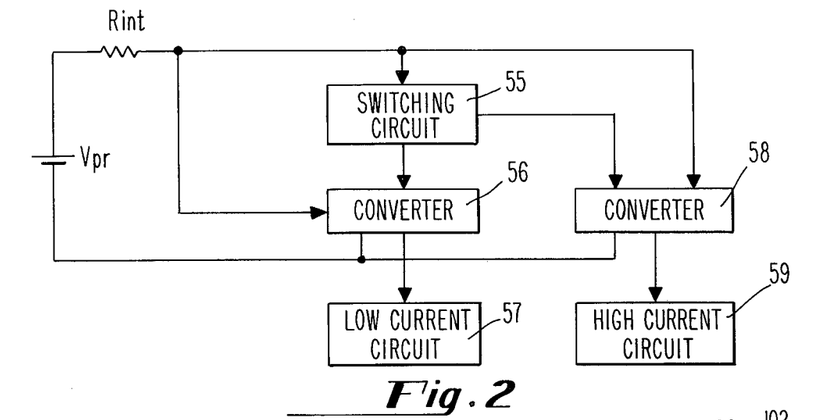
FIG. 2 is a block diagram showing the switching arrangement of FIG. 1 in combination with converters for providing converted voltage levels to respective different circuit portions.

Referring now to FIG. 2, there is shown a block diagram which differs from heat that of FIG. 1 by the inclusion of converters 56 and 58 positioned between switching circuit 55, and the low current circuit 57 and high current circuit 59 respectively. In this arrangement, the effect of the switching circuit is the same, and in addition the converters provide a raised DC voltage to the respective circuits. As is seen in the following discussion of the circuit of FIG. 3, the converter includes means for temporarily storing energy which is transferred from the source through the switching circuit. Each of the converters 56 and 58 suitably receives energy from the source periodically at a rate determined by switching circuit 55, converts the energy to a higher level DC, and provides it to its respective circuit. The voltage received by converter 56 is substantially independent of the current drain to circuit 59, such that the voltage delivered to the voltage sensitive circuit 57 is, throughout most of the lifetime of operation of the system, substantially unaffected by the loading of circuit 59. It is to be noted that for both the arrangements of FIG. 1 and FIG. 2 the limit in the lifetime of operation will be primarily determined by the energy depletion caused by the loading of the high current circuit. When such energy depletion has proceeded to the point where the $R_{int}$ is so great that not enough current can be delivered to the high current circuit, then the useful lifetime of the system is at hand.

Figure 3:
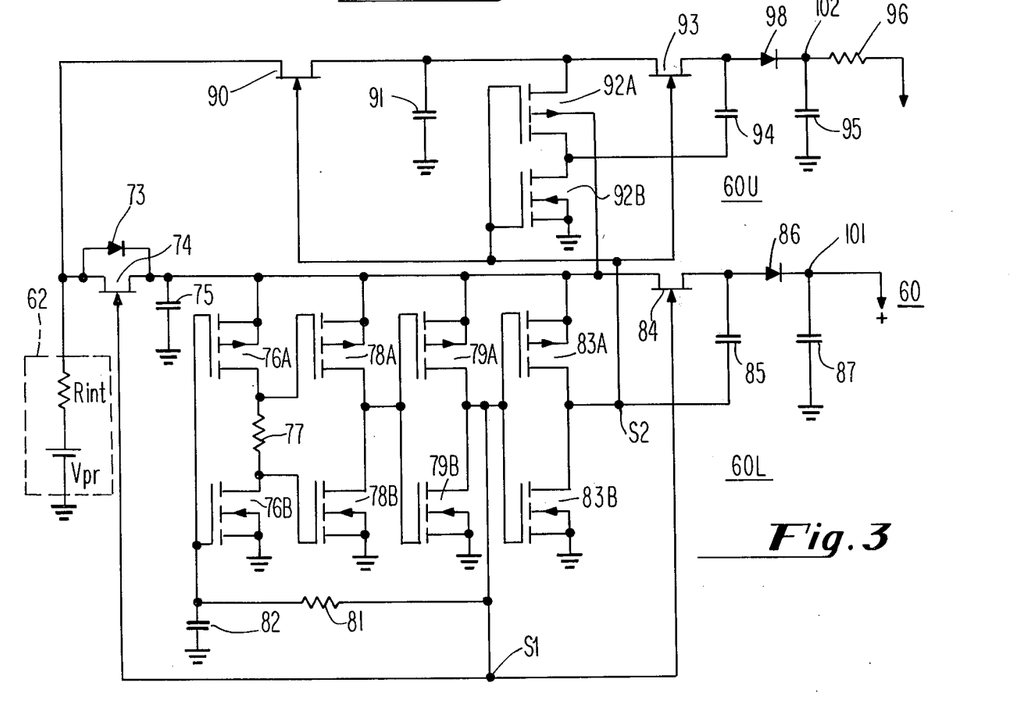
FIG. 3 is a circuit diagram of the preferred embodiment of this invention.
Figure 7:
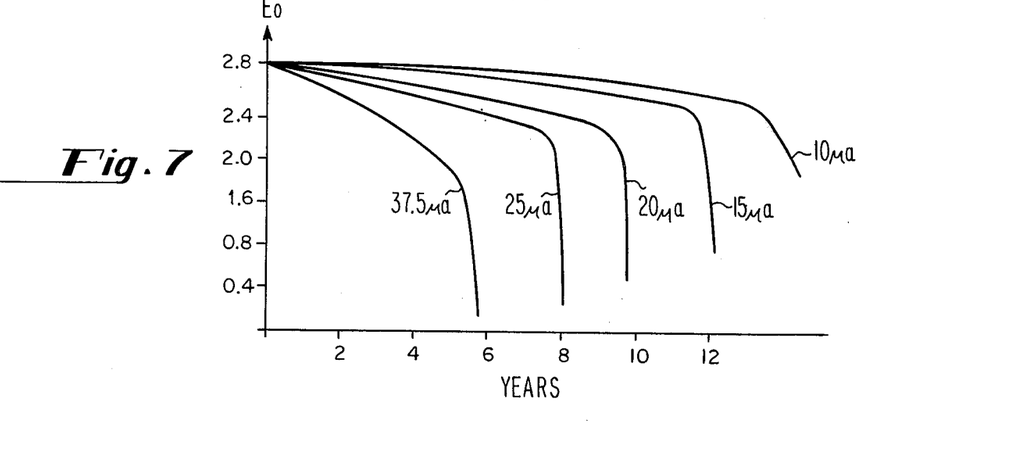
FIG. 7 is a second set of curves illustrating typical characteristics of a source as utilized in this invention.

Referring now to FIG. 3, there is shown a detailed circuit diagram of a circuit which represents a preferred embodiment of the apparatus of this invention. The switcher/converter circuit 60 of FIG. 3 is part of an overall pacer such as illustrated in FIG. 5. The source 62 is represented by a voltage source which for a typical lithium cell is 2.8 volts. The internal resistance is a function of the energy depletion of the cell, as illustrated in FIG. 6. In this specification, the terms energy depletion and power depletion are used synonymously, indicating the condition where power has been transferred from the battery, thereby depletion the power or energy available for future transfer from the source to the circuit which it is driving. The energy depletion is, of course, a function of the average current drain, and the curves of both FIG. 6 and FIG. 7 represent the changing source characteristics as a function of time, where different values of average current drain are presented as parameters.

Source 62 is connected through diode 73 and FET 74 to a first step up, or booster capacitor 75. The nongrounded side of capacitor 75 is connected to ground through 4 CMOS pairs, the 4 pairs comprising FET portions 76A–76B, 76A–78B, 79A–79B, and 83–83B. The gates of 76A and 76B are connected together and through capacitor 82 to ground. The drain of 76A is connected through high resistance 77 to the drain of 76B, with the drain of 76A connected to the gate of 78A and the drain of 76B connected to the gate of 78B. The drains of 78A and 78B are connected together to the gates of 79A and 79B, the drains of 79A and 79B being connected together to the gates of 83A and 83B at node S1. The drains of 83A and 83B are connected together at node S2. S1 is connected through resistor 81 and capacitor 82 to ground, forming a timing path for timing of the oscillator formed by the first 3 CMOS pairs. Node S1 is also connected to the gate of FET 74. The junction of capacitor 75 and FET 74 is connected to FET 84, which has its gate connected at node S1. The output of FET 84 is connected through capacitor 85 to node S2, and through diode 86 and storage capacitor 87 to ground. Terminal 101, which carries the voltage across capacitor 87, is the output terminal of the converter on the bottom path of FIG. 3.

The upper path of FIG. 3 comprises FETs 90 and 93 which have gates connected to node S2, and are switched on or off depending upon the signal level at node S2. Connected between FET 90 and ground is a first step up capacitor 91, and FET pair 92A–92B, having common gates connected to node S2. The drains of 92A and 92B are tied together through second step up capacitor 94 to the output of FET 93. The junction between FET 93 and capacitor 94 is connected to ground through diode 98 and storage capacitor 95. The voltage across capacitor 95 is connected through resistor 96 to the collector of output drive transistor 108 (see FIG. 5), this being the high current circuit.

In operation, at startup timing capacitor 82 is uncharged, so the gate of MOS-FET 76A is low, causing it to conduct. The starting current is provided through diode 73. While capacitor 82 is charging, MOS-FET 78A is off since the drain of 76A is high, and MOS-FET 78B is on, so that the gates of 79A and 79B are low. Under these conditions, S1 is high and S2 is low, such that the lower path FETs 74 and 84 conduct and the upper path FETs 90 and 93 are non-conducting. Under these conditions, capacitor 75 charges through FET 74, and capacitor 85 charges through FETs 74 and 84 and MOS-FET 83B. Capacitor 82 proceeds to charge through MOS-FET 79A and resistor 81, until it attains a voltage high enough to switch the first CMOS pair 76A–76B. When this happens, each of the subsequent CMOS pairs switches, reslting in the condition where S1 is low and S2 is high, such that the upper path FETs are conducting and the lower path FETs are non-conducting. It is noted that at the moment of switching, the current through CMOS pair 76A–76B is limited by the high value resistor 77. Since this first CMOS pair receives the switching signal developed across capacitor 82 and is the slowest switching pair, the high resistance is significant in limiting the current during switching, and reducing the power drain of the switching oscillator. Also, at the moment of switching capacitors 75 and 85 have been charged to substantially the voltage output of the source, i.e., about to $V_{pr}$. FETs 74 and 84 switch off when timing capacitor 82 has discharged through resistor 81 and MOS-FET 79B to the point where 76A and 76B are switched.

At the time of oscillator switching, a series path is formed comprising capacitor 75, MOS-FET 83A, step up capacitor 85, diode 86 and storage capacitor 87. The two step up capacitors, each charged substantially to $V_{pr}$, are in series and placed across storage capacitor 87, such that they act to charge capacitor 87 up to a value of two times $V_{pr}$. Thus, once each cycle of the oscillator frequency, the two step up (or booster) capacitors supply an additional incremental amount of energy through to the storage capacitor 87, the process repeating until capacitor 87 attains appreciably a voltage of 2 times $V_{pr}$.

In the upper path, when FETs 90 and 93 conduct, the lower MOS-FET 92B is conducting, such that both capacitors 94 and 91 are placed between the source and ground. Upon switching at node S2, a series path is established comprising capacitor 91, MOS-FET 92A, capacitor 94, diode 98 and capacitor 95. In a like manner as described for the lower path, the two booster capacitors are placed in series and act to charge the storage capacitor 95 to appreciably two times $V_{pr}$. The output of capacitor 95 is connected through a resistor 96 to the collector of output transistor 108, as seen in FIG. 5.

The cycle is repeated each time capacitor 82 charges or discharges to the point where the CMOS pairs in the lower circuit are switched. Thus, both lower path 60L and upper path 60U switch back and forth, being in alternate states such that when one is drawing power from source 62 the other is transferring it to its storage capacitor, and vice versa.

The following table lists typical values of elements shown in FIG. 3. It is to be understood that these values are illustrative of a working embodiment, and are not limiting. In particular, the values of those elements which affect the conversion characteristic, i.e., the multiple by which the converter raises the DC level as a function of source condition, may be chosen in accordance with the desired programmed characteristic.

TABLE I

| Capacitors 76, 85, 91, 94 | $33 \times 10^{-12}$f |
|---|---|
| Capacitors 87, 95 | $4.7 \times 10^{-6}$f |
| Resistor 81: | 1 Megohm |
| Resistor 77: | 10 Megohm |
| Resistance 96: | 27 Kilohm |
| FETs 74, 84, 90, 93: | type 2N4338 |
| Diodes 86, 98: | type 1N5711 |
| Diode 73: | type 1N35gs |
| CMOS: | type CD4007A |

While the circuit as shown in FIG. 3 is a preferred embodiment, it is noted that design changes can be made to achieve different operating characteristics, within the scope of this invention. Typical of such changes are those discussed hereinbelow in connection with variations of circuit operation with changes in switching oscillator frequency and duty cycle.

Figure 4:
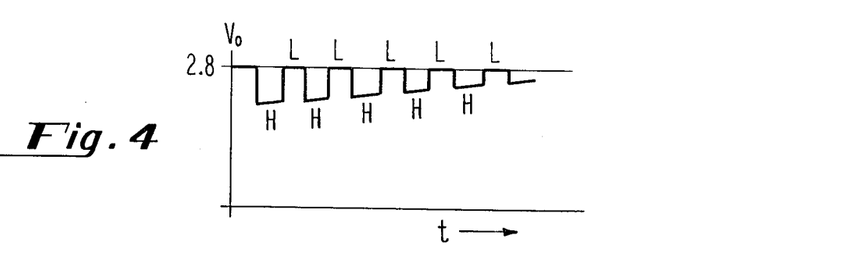
FIG. 4 is a graph illustrating the voltage level at the source output for the circuit of FIG. 3.

Referring now to FIGS. 4 and 5, the utility of the invention in terms of shielding the loading effect of the stimulus delivery circuit from the operation of the stimulus pulse oscillator, can be observed. FIG. 4 illustrates the voltage output at the terminals of source 62 when the source is used to power the pacer of FIG. 5. FIG. 5 is a block diagram of a pacer as disclosed in my previously referenced co-pending application Ser. No. 608,465. In this circuit, the lower converter outlet 101 is connected to the amplifier, the logic circuitry, and the stimulus pulse oscillator, all of these being relatively low current drain circuit portions. Node 102, the output of the upper converter path, is connected through resistor 96 to the collector of output transistor 98 and to output capacitor 97. When transistor 108 is gated to conduction by stimulus oscillator 68 it provides a discharge path through capacitor 97, resulting in a pulse across the electrode which is shown as load resistor $R_L$. Diode 99 limits the stimulus pulse to a predetermined value. It is to be noted that the exact connection of the low current and high current converters may differ, the important point being that the voltage sensitive oscillator circuit 68 is driven by a converter which is in alternate switching connection with the source as compared to the converter which supplies the high current circuit. The high current circuit comprises at least the output circuit for delivering the high current stimulus pulses, but may include other circuit portions. An important function of the switching circuit is to arrange the circuit independence of the voltage sensitive circuit from the high load circuit. By the term independence it is meant that the current drain of the high current circuit has no effect on the source when and as power is being delivered from the source to the voltage sensitive circuit. Of course, in the long run the current drain of the high current circuit causes energy depletion which results ultimately in change of the operation of the voltage sensitive circuit. However, whatever the state of depletion of the source, the voltage which is delivered to the voltage sensitive circuit is a function only of the source and the current drain of the low current circuit, and is independent of the contemporary current drain of the high current circuit. Indeed, since the low current circuit drain is typically 5 microamps or less, as long as the battery source is on the linear portion of its characteristic it can be said that the loading of the high current circuit has had no practical effect on the stimulus oscillator operation.

Referring to FIG. 4, there is shown a plot of the voltage variations, i.e., variations of $V_o$, at the output of the source 62. The periods when the low current drain converter is operating are designated by the letter L, and the periods when the high current drain converter is operating are designated by the letter H. For the graph shown, it is assumed that a stimulus pulse has just been delivered, and that storage capacitor 95 is recharging. In the absence of the switching function, this capacitor would charge up roughly exponentially in accordance with the time constant determined by the value of the capacitor and the value of the internal resistance. The voltage drops designated H represent the drop across the internal resistance caused by the charging current. As the internal resistance of the source increases with lifetime, the loading effect is magnified and the pulses drop. During the times when the low current converter is drawing current, the current drain is substantially negligible, such that the voltage is maintained at about 2.8 volts. The frequency of the pulses illustrated in FIG. 4 is determined by the oscillator of circuit 60. Since the rate of stimulus oscillator 68 is determined by the voltage source which powers it, it is clear that in the absence of switching the rate would be affected by the loading of the output circuit. However, with the pacer of this invention, the oscillator 68 sees the source only at the times L, and consequently doesn't see the high current loading, except as an extremely small secondary effect. This result is further illustrated by the test results in Table II below.

Figure 8:
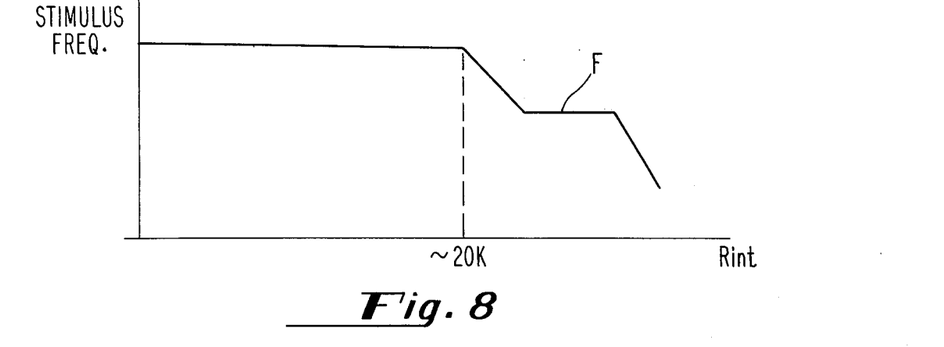
FIG. 8 is a graph illustrating the frequency characteristics of the stimulus generator of the pacer of this invention.

In circuit 60 of FIG. 3, the values of the booster capacitors 75 and 85, and the frequency of the switching oscillator, are important design parameters in conjunction with the characteristics of the source 62. In order to maintain a substantially constant voltage across storage capacitor 87, booster capacitors 75 and 85 must be charged to substantially $V_{pr}$ during each charging cycle. This is accomplished so long as the RC time constant determined by the internal resistance of the source and the booster capacitor is sufficiently small compared to the charging period, which latter period is determined by the oscillator frequency. It is to be noted, of course, that the charging period could be altered either by changing the combination of resistor 81 and capacitor 82, or by changing the duty cycle of the oscillator. In any event, when the combination is such that the booster capacitors do not get fully charged during the charging time period, storage capacitor 87 drops in voltage. As the battery is depleted further, causing the internal resistance to become greater, the charging each cycle is less and less, such that there results a drop off in the voltage delivered by the converter. For the typical parameter values as set forth in Table I, it has been determined that a pacer such as shown in FIG. 4, incorporating the switching circuit 60 as shown in FIG. 3, has output frequency characteristics substantially as shown in FIG. 8. The curve of FIG. 8 is based upon an average pacer current drain of 25 microamps, as can be seen by comparison with FIG. 6. It is noted that for any given average current drain, the source characteristics are substantially linear until a knee is reached, at which point the characteristics change drastically due to depletion. For the example of a 25 microamp average drain, at about 8 years lifetime $R_{int}$ increases sharply, and the output voltage drops almost vertically. The design criteria, of course, is to utilize to the fullest possible extent the linear portion of the curve before the knee where the battery characteristics change relatively little.

In tests performed on the pacer of FIG. 3, it has been observed that, at the point where the internal resistance rises to a value such that less than 2.4 volts is provided, the frequency response curve flattens out for a segment. See segment F of FIG. 8. Tests on the circuit indicate that the oscillator has a frequency peak at a supply voltage of $2 \times V_p$ (about 2.6 volts), and works with voltages down to about 1.5 volts with only a frequency decrease.

The effect of the converter switching frequency on the conversion characteristics, and thus on the stimulus generator rate, has been tested, with results as shown in Table II. For the results listed, $R_L$ was 1 Kilohm.

It is to be noted that, for the ranges of $R_{int}$ tested, stimulus rate variations were relatively limited. This confirms the utility of the circuit in providing programmed reliable stimulus generation through to the knee of the source characteristics.

TABLE II

| | Switching Frequency, 500 Hz | |
|---|---|---|
| $R_{int}$ (Kilohms) | Stimulus Rate (ms) | Pulse Width (ms) |
| 0 | 868.2 | 0.996 |
| 10 | 871.3 | 1.007 |
| 20 | 878.3 | 1.028 |
| 27 | 883.6 | 1.044 |

| | Switching Frequency, 1.1 KHz | |
|---|---|---|
| $R_{int}$ (Kilohms) | Stimulus Rate (ms) | Pulse Width (ms) |
| 0 | 867.5 | 1.003 |
| 10 | 876.1 | 1.024 |
| 20 | 886.1 | 1.054 |
| 27 | 893.6 | 1.078 |

| | Switching Frequency, 2.5 KHz | |
|---|---|---|
| $R_{int}$ (Kilohms) | Stimulus Rate (ms) | Pulse Width (ms) |
| 0 | 864.7 | 0.998 |
| 10 | 876.5 | 1.026 |
| 20 | 888.0 | 1.061 |
| 27 | 896.6 | 1.090 |

Tests have also been performed to determine circuit performance where the battery source impedance contains a capacitive component. For a capacitance of 10 kpf across the source terminals, only a slight change in circuit performance was measured. The observed variation of stimulus rate as a function of switching frequency illustrates the fact that the conversion multiple has a characteristic which is programmable. Assuming that the stimulus rate varies linearly with the voltage delivered by the converter, the curve of FIG. 8 represents approximately the variation of the conversion multiple as a function of source energy depletion. The conversion multiple can be programmed for the circuit of FIG. 3 by design of the switching frequency or the booster capacitors. Note that the booster capacitors could be designed of different values for the two converter circuits, so as to provide a different conversion characteristic for each converter. Additional circuit modifications for programming the conversion characteristic are a matter of design choice, and within the scope of this invention. For use in a cardiac pacer, the conversion characteristic is preferably continuous, so that there is no sharp reduction in pacer rate at any point of battery depletion.

Figure 9A:
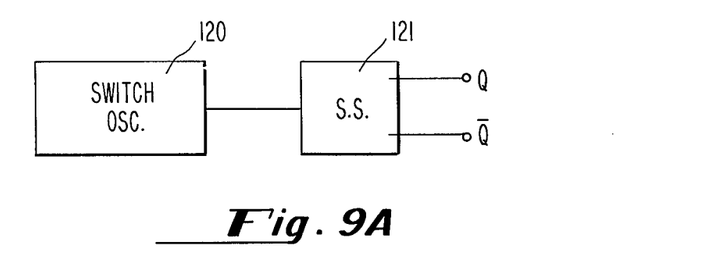
FIG. 9A is a simplified block diagram showing a circuit for achieving a desired duty cycle for the switching oscillator of FIG. 3.
Figure 9B:
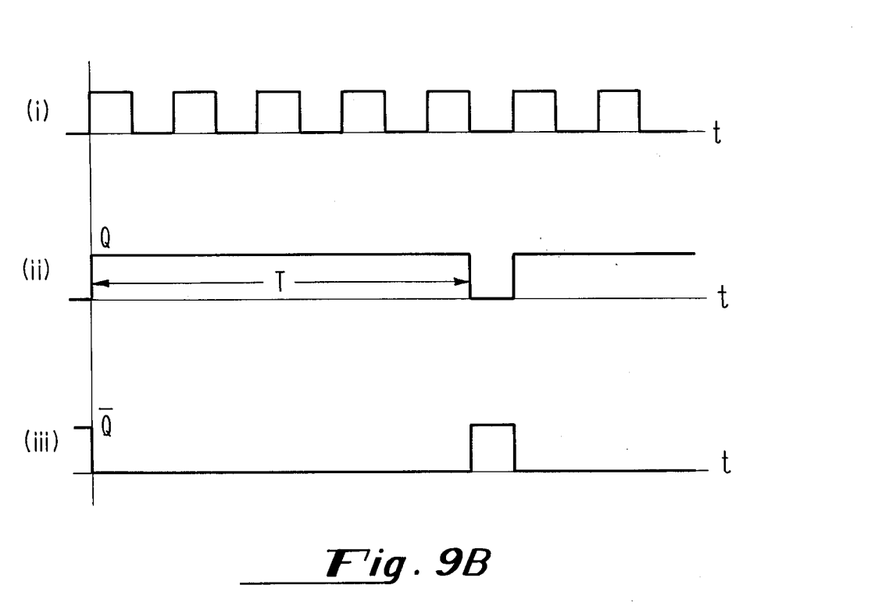
FIG. 9B is a set of curves illustrating the wave forms generated by the circuit of FIG. 9A.

Referring now to FIGS. 9A and 9B, an embodiment of the circuit of FIG. 3 is shown which is adaptable to provide improved matching of the device circuits to the power source. Instead of having only a switching oscillator, a switching oscillator 120 is used in combination with a single shot circuit 121 of conventional form. Circuit 121 provides two outputs, as shown designated Q and $\bar{Q}$ which are connected to respective circuit portions, e.g., a high power circuit portion and a low power circuit portion. The purpose of the single shot, or any equivalent logic circuitry which may be utilized, is to provide an output having a duty cycle programmed to better match the respective circuit portions to the power source. As shown in FIG. 9B, the switching oscillator 120 may produce a symmetrical signal as shown in curve (i). The output of oscillator 120 is fed into single shot circuit 121, which may suitably be triggered by an upward going input and, once triggered, maintains a changed state for a predetermined period of time such as designated T in curve (ii). As illustrated in curves (ii) and (iii) the output of Q is high for a time period illustrated as being 9 times as long as the time period during which $\bar{Q}$ is high. Clearly, by adjusting the single shot circuit, this ratio can be adjusted in any desired manner. As used in a pacer, the output from node Q would suitably be connected to the high power circuit, and the output from node $\bar{Q}$ would be connected to the low power, or voltage sensitive circuit. In this manner, the high power drain circuit has more opportunity to charge up to the desired power or voltage level, whereas the low power circuit can obtain its power needs during the shorter time interval. By simply setting the time duration of the single shot or equivalent logic circuit, the duty cycle can be varied according to the tested relative power demands of the different circuit portions.

Figure 10:
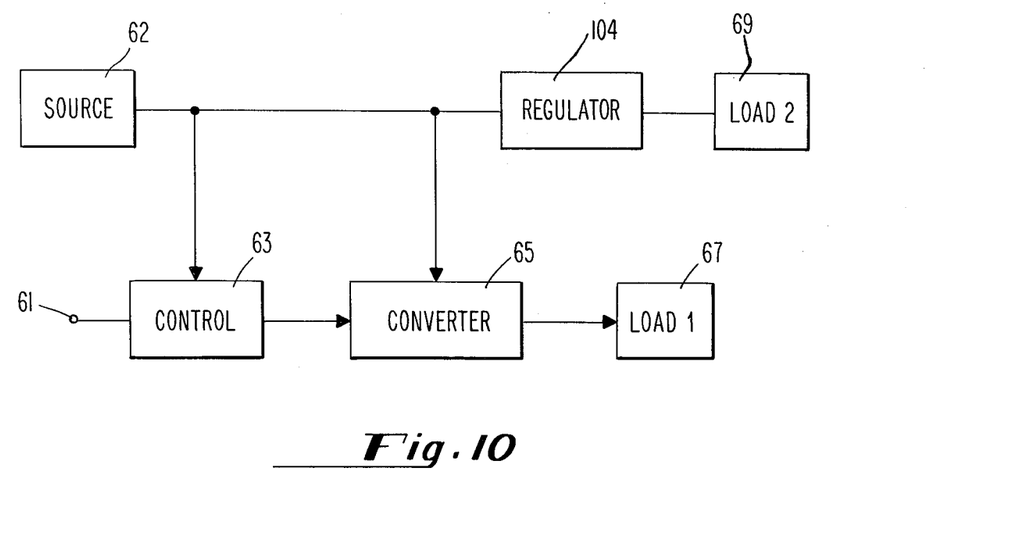
FIG. 10 is a block diagram of an alternate embodiment of this invention.

Referring now to FIG. 10, there is shown a block diagram of an alternate embodiment of this invention, which represents a variation of FIG. 5. Source 62 is shown connected to and driving a converter 65, which in turn drives load 1 designated at block 67. A second load, designated at block 69, can be driven directly from the source, without a converter. This is the case, for example, if in FIG. 5 the output of source 62 is connected directly to resistor 96, without any conversion involved. Or, conversely, converter output 101 may be connected directly to resistor 96 to drive the high load output, and the battery output may be connected directly to the remaining circuitry. In this embodiment, the variation of the conversion characteristic as a function of the condition of source 62 is represented by control block 63. Conversion control may be programmed, for example, by changing either booster capacitor 75 or 85, the requency of the oscillator or the duty cycle of the oscillator, or any combination of these. In addition, control circuit 63 may include means for directly indicating the source condition, as illustrated by node 61. Further, if load 2 includes a high current circuit, a regulator 104 may be positioned between source 62 and the load.

Figure 11:
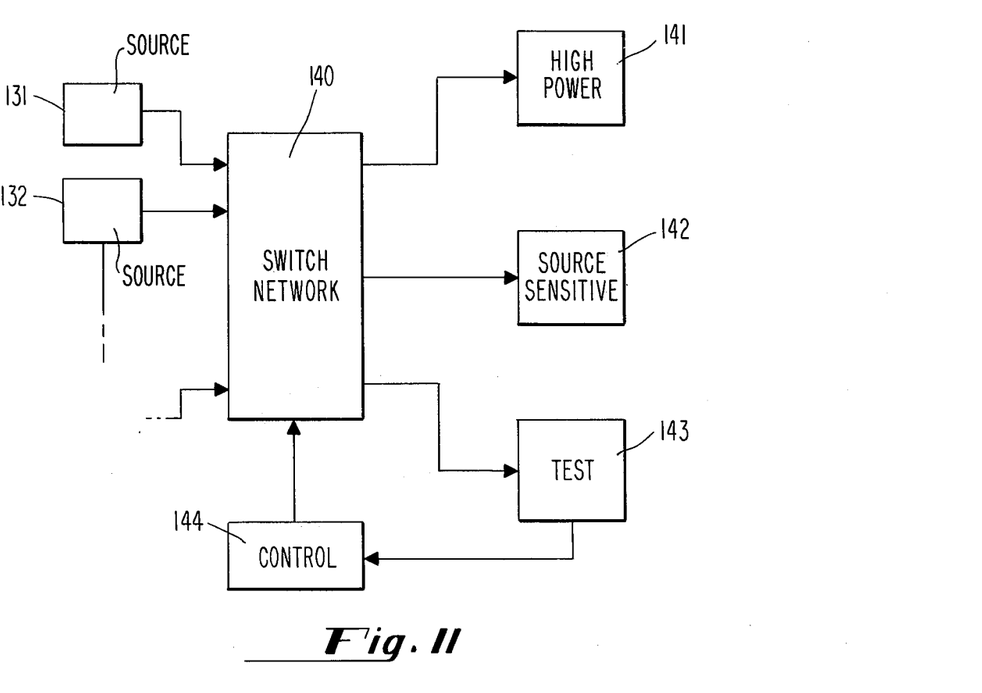
FIG. 11 is a block diagram of another embodiment of the switching power delivery means of this invention.

Referring now to FIG. 11, there is shown a block diagram of another embodiment of this invention illustrating use of the switching network to switch a plurality of sources into connection with respective different circuit portions. Two sources 131 and 132 are shown connected to the switching network 140 which may suitably comprise switching circuitry such as illustrated in FIG. 3. Although just two sources are shown, it is to be understood that any number of sources could be connected to the switching network. Network 140 has a suitable number of switching paths, enabled or disenabled by switch control 144, connecting to its output any one of the input sources. In the alternative, the switching network 140 may be designed with conventional logic to time multiplex 2 or more of the input sources, so that at any given period of operation 2 or more of the input sources may be providing power to the output circuits. The outputs of network 140 are connected to a plurality of circuit portions, FIG. 11 illustrating 3 such portions. Portion 141 is illustrated as a high power portion, and is connected through network 140 to a source or sources for a fraction of time determined to provide maximum power or energy transfer. Circuit portion 142 is designated as a source sensitive portion, and is connected through switching network 140 to a source or sources for a fraction of time designed to best match the available source current or voltage to its current or voltage needs. Circuit 143 is indicated as being a test circuit, and may be periodically connected to one or more of the sources to determine the condition of such source or sources. For example, the test circuit may test for voltage levels, current delivery to a predetermined load, etc. The test circuit is suitably designed to provide control signals to switch control network 144, which in turn is programmed to control 140 so as to connect through to the desired source or sources. For example, in a pacer environment, source 1 may be a primary battery which is used for the major portion of the pacer lifetime, while source 2 may be a lower energy backup battery which is switched into service when the primary source is tested to have fallen below predetermined allowable limits. At such time, source 1 may be switched out of operation and source 2 switched in, or the sources themselves may be time multiplexed through the switching network to the different circuit portions. Additionally, it is understood that if any one or all of the circuit portions require a higher voltage or current than would be available directly from the source or sources being utilized, appropriate converters may be incorporated into this embodiment.

In summary, the invention disclosed is highly versatile in interfacing the desired electronic circuitry of an apparatus such as a cardiac pacer to the characteristics of the power source. The switching power delivery network provides for matching the differing power, voltage or current requirements of different circuit portions to the available source or sources. By this means, source sensitive circuit portions may be shielded from the concurrent loading effect of other circuit portions so as to optimize circuit performance. The invention provides for conversion of the DC level of the source to a value or values suitable for driving the entire circuit or respective portions of the circuit. Further, the conversion factor, or multiple by which the source voltage is raised, it programmed to vary in a predetermined manner as a function of the changing source characteristics. In the preferred embodiment presented, the programming is achieved by incorporating circuit components which interact with the changing internal resistance of the source. Alternatively, for a source where the internal resistance is substantially constant and the ideal voltage value is subject to change, the circuit may be modified to produce a different conversion multiple as a function of the changing voltage. While the circuit illustrated has embodied a voltage sensitive circuit, the invention also covers current sensitive circuits, and for this reason the sensitive circuit may be referred to as being source sensitive. The voltage sensitive circuit may have operating characteristics which vary as a function of delivered voltage, as in the case of the variations in stimulus pulse rate of the oscillator of a cardiac pacer. Within the meaning of a voltage sensitive circuit, however, is included any circuit which is designed to either detect a changing voltage or operate as a function of a changing voltage, and which gives either a direct or indirect indication of such changing voltage.

As used herein, the terms battery and battery source are defined as meaning an electrical source having a limited energy supply. The most common form of battery source has an initial energy supply which when expended is not replenished from any other source. In addition, a battery source may be of a type such as the bio-galvanic cell which is able to replenish some of its expended or depleted energy. In all such cases, the battery source has a finite lifetime, or has characteristics which change as a function of its use and lifetime, or both.

The preferred embodiments as described are seen to fulfill the above objects of the invention. While the invention is particularly suitable for cardiac pacing systems, it is also suitable for other systems requiring optimization of the interface between a DC power source and the electrical load being driven by the source. The types of sources embraced by this invention are varied, as are the types of loads. The invention is equally effective in all types of pacing systems, i.e., synchronous, demand, etc., and with all types of catheters or electrodes. It is likewise effective particularly for other low power self-contained devices, e.g., digital watches, where improvement can be obtained by matching of respective different circuit portions to the source or sources. While the pacer embodiment illustrated utilizes a converter, the embodiment without a converter is applicable wherever conversion is not required. By way of example, and without limitation, in future pacer designs injected logic (IIL) or other techniques may be utilized permitting circuit operation well below 2.8 volts.

I claim:

1. Self contained pacer apparatus for delivering stimulus pulses, comprising:
    a. a battery source which provides an output which varies with the loading thereof and having characteristics which vary as a function of its energy depletion;

b. a source sensitive stimulus pulse generating circuit;

c. a stimulus output circuit, driven by the output of said source sensitive circuit, for delivering said stimulus pulses; and d. connecting means for connecting said source output respectively to said source sensitive circuit and to said stimulus output circuit so that the loading of each of said circuits has no effect upon said source output when connected to the other of said circuits.

2. The apparatus as described in claim 1, wherein said connecting means comprises switching circuitry for delivering power to only one of said circuits at a time.

3. The apparatus as described in claim 2, wherein said switching circuitry contains an oscillator.

4. The apparatus as described in claim 1, wherein said source has an internal resistance which varies as a function of said energy depletion, and wherein said connecting means comprises conversion means for converting the potential level of said source to a higher potential, said conversion function varying as a function of said internal resistance.

5. The pacer of claim 1, wherein said connecting means connects said circuits to said source so that only one of said two circuits loads said source at any given time.

6. Self contained pacer apparatus for producing stimulus pulses, comprising:

a. a source having characteristics which vary as a function of its energy depletion;

b. first temporary power storage means for storing power transferred to it from said source;

c. second temporary power storage means for storing power transferred to it from said source;

d. transfer means for controlling the transfer of power from said source to said first and second storage means respectively so that such transfer is to only one of said storage means at a time; and e. pacer circuitry for producing said stimulus pulses, having a first circuit portion connected to said first storage means and a second circuit portion connected to said second storage means.

7. The apparatus as described in claim 6, wherein said transfer means comprises means for inhibiting transfer to said second storage means when tranfer is taking place to said first storage means.

8. The apparatus as described in claim 6, wherein each of said storage means comprises means for raising the DC level of said tranferred power.

9. The apparatus as described in claim 8, wherein said first circuit portion includes a circuit for generating stimulus signals at a programmed rate, and said second portion includes a circuit for delivering said stimulus pulses.

10. The apparatus as described in claim 9, wherein said transfer means cooperates with each of said storage means so that the converted voltage level at the output of each of said storage means is in accordance with a predetermined respective conversion characteristic.

11. The apparatus as described in claim 10, wherein said conversion characteristic is a function of said energy depletion, and is a continuous characteristic.

12. A cardiac pacer for operation in combination with an electrode for delivery of stimulus pulses to a patient's heart, comprising:

a. a power source having characteristics which vary as a function of its energy depletion;

b. A voltage sensitive circuit, including a stinulus signal generator;

c. a high current circuit, including a stimulus signal output circuit driven by said stimulus signal generator;

d. a first converter switchably connected to said power source;

e. a second converter switchably connected to said power source;

f. a switching oscillator;

g. switch connecting means connected to receive inputs from said oscillator, for switchably connecting said power source to said converters so that (i) when said first converter receives power from said source said second converter is inhibited from receiving power said source and so that (ii) when said second converter receives power from said sourve said first converter is inhibited from receiving power from said source; and h. second connecting means for connecting said first converter to said voltage sensitive circuit and said second converter to said high current circuit, whereby the relatively high current drain of said high current circuit does not load said source while power is being transferred from said source to said first converting ciruit.

13. The pacer as described in claim 12, wherein said switching oscillator comprises CMOS devices.

14. The pacer as described in claim 13, wherein said CMOS oscillator comprises a CMOS pair with gates connected in common and a high resistance connected between the drain of one and the drain of the other.

15. The pacer as described in claim 12, wherein said source has an internal resistance which varies as a function of said energy depletion, and said first converter comprises a pair of step up capacitors, the capacitance of at least one of said step up capacitors and the frequency of said switching oscillator being predetermined to program the conversion characteristics of said first converter as a function of said source internal resistance.

16. The pacer as described in claim 15, wherein said second converter has a pair of step up capacitors, and the capacitance of at least one of said step up capacitors and the frequency of said switching oscillator are predetermined to program the conversion characteristics of said second converter as a function of said source internal resistance.

17. The pacer as described in claim 16, wherein said switch connecting means comprises respective FETs connected to opposite polarity outputs from said switching oscillator.

18. An implantable cardiac pacer for providing stimulus pulses for stimulating the heart of a patient, said pacer being adapted to produce said stimulus pulses at a rate which is variable as a function of the condition of its power source, comprising:

a. a DC power source having characteristics subject to variation as a function of its energy depletion;

b. programmable converting means for converting the DC output of said source to a higher DC level, said converting means being powered by said source and providing a conversion which is a programmed function of said source characteristics;

c. pulse generation means having at last a portion connected to said converting means, for generating stimulus pulses at a rate which is a predetermined programmed function of the DC level delivered by said converting means; and d. said pulse generation means and converting means being programmed so that said pulse generation rate is a predetermined funtion of said source characteristics.

19. The pacer as described in claim 18, wherein said source is characterized by having an internal resistance which varies as a function of its energy depletion, and said converting means is programmed to provide a DC voltage conversion which is a function of said internal resistance.

20. The pacer as described in claim 19, wherein said converting means provides a DC output level which is a variable multiple of said source DC level, and having means for varying said multiple as a function of said source characteristics.

21. The pacer as described in claim 18, wherein said pulse generation means comprises a stimulus signal generator portion and a stimulus signal delivery portion, and said converting means comprises a first converting means powering said generator portion and a second converting means powdered by said source for providing a second conversion of said DC output of said source to a higher DC level, said second conversion also being a programmed function of said source characteristics, said second converting means powering said delivery portion.

22. The pacer as described in claim 21, wherein said converting means comprises switching means for alternately connecting said first and second converting means to said source.

23. The pacer as described in claim 22, wherein said converting means comprises a switching circuit which switchably connects only one of said first and second converting means to said source at a time.

24. An electromedical system comprising a stimulus generator for use in combination with an electrode, for generation of stimulus pulses, wherein said stimulus generator comprises:

a. a DC power source which provides an output which is a variable as a function of the load it supplies;

b. a plurality of circuits each powered from said power source, including a source sensitive circuit which normally draws a first predetermined current and a second circuit which produces said stimulus pulses and which normally draws a second predetermined current; and c. means for delivering power from said source to each of said circuits in a manner so that the source output is not effected by the loading of said second circuit when said source is delivering power to said source sensitive circuit.

25. The system as described in claim 24, wherein said power delivering means further comprises means for converting the DC voltage level of said source to a higher level, and delivering power at said higher DC level to at least one of said plurality of circuits.

26. The system as described in claim 24, wherein said power delivering means delivers power to each of said circuits periodically at a predetermined rate.

27. A method carried out in a biomedical stimulus delivery system, said system having a DC power source, a relatively low current circuit and a relatively high current circuit for generating and delivering stimulus signals, said method comprising:

a. transferring energy alternately from said DC source and storing said transferred energies in respective first and second storage circuits of said system;

b. transferring said stored energies alternately to said low current and high current circuits respectively, whereby the energy being transferred to said relatively low current circuit is independent of the energy being transferred to said high current circuit;

c. generating stimulus signals; and d. delivering said generated signals from said high current circuit.

28. The method as described in claim 27, wherein said system is an implantable cardiac pacing system and said source is a battery source, and comprising raising the voltage level of the energy delivered to said low current circuit.

29. Self-contained pacer apparatus for delivering stimulus pulses, comprising:

a. a battery;

b. a first circuit portion for delivery of stimulus pulses, and a second circuit portion for proviing signals to said first circuit portion; and c. means driven by said battery for switchably delivering power from said battery to said first and second circuit portions, whereby each of said circuit portions receives delivered power periodically for alternate different time periods.

30. The pacer apparatus as described in claim 29, wherein said means for delivering comprises oscillator means for producing a periodic signal having a perdetermined duty cycle.

31. The pacer apparatus as described in claim 30, wherein said means for delivering comprises a converter circuir connected to said oscillator for converting the voltage level of the power delivered to at least one of said circuit portions, said converter circuit having a conversion characteristic which is a function of said predetermined duty cycle.

32. The pacer apparatus as described in claim 31, wherein said oscillator comprises a plurality of interconnected CMOS pairs of active elements, timing means for developing a switching signal at predetermined time intervals, said timing means output being connected to the input of one of said CMOS pairs, and said one CMOS pair having a high resistance connected between its two active elements.

33. The pacer apparatus as described in claim 31 wherein said oscillator means comprises an adjusting circuit for adjusting said periodic signal to be asymmetric in accordance with said predetermined duty cycle.

34. Self-contained pacer apparatus for delivering stimulus pulses, comprising:

a. a battery;

b. a first circuit portion for delivery of stimulus pulses, and a second circuit portion for providing beat rate signals to said first circuit portion; and c. a switching circuit hving two switching paths, the first of said paths having a first path input connected to said battery, a first path output connected to said first portion and a first switching element, the second of said paths having a second path input connected to said battery, a second path output connected to said second portion and a second switching element, said switching circuit having an oscillator producing periodic switching signals of opposite polarities, and a connecting circuit connecting a first of said switching signals to said first switching element whereby it is driven alternately closed and open and the second of said switching signals to said second switching element whereby it is driven alternately open and closed, whereby power from said battery is delivered alternately to said first and second circuit portions.

35. The pacer apparatus as described in claim 34, comprising means for adjusting the duty cycle of the periodic switching signals.

36. The pacer apparatus as described in claim 35, wherein said adjusting means is set so that said first and second switching elements are closed for unequal periodic time periods.

37. The pacer apparatus as described in claim 35, wherein said battery has an internal resistance that varies as a function of its state of energy depletion, and said duty cycle means is adjusted so that said power delivery means and said first and second circuit portions cooperate so that the beat rate of said stimulus pulses is representative of the value of said internal resistance.

38. The pacer apparatus as described in claim 37, wherein said power delivery means comprises a conversion means in at least one of said paths for convering the voltage level of said battery by a multiple which is a function of said internal resistance.

* * * * *

UNITED STATES PATENT AND TRADEMARK OFFICE
CERTIFICATE OF CORRECTION

PATENT NO. : 4,031,899
DATED : June 28, 1977
INVENTOR(S) : Alexis C. M. Renirie

It is certified that error appears in the above-identified patent and that said Letters Patent are hereby corrected as shown below:

Column 5, line 14, delete "pace" and insert therefor --pacer--.
Column 5, line 14, delete "stimular" and insert therefor --stimulus--.
Column 7, line 7, delete "heat".
Column 7, line 57, after "83" first occurrence, insert --A--.
Column 13, line 5, delete "requency" and insert therefor --frequency--.
Column 14, line 9, delete "it" and insert therefor --is--.
Column 16, line 21, after "power" insert --from--.
Column 17, line 58, change "effected" to --affected--.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*